United States Patent
Piazza et al.

(10) Patent No.: US 10,127,657 B2
(45) Date of Patent: Nov. 13, 2018

(54) SYSTEM AND METHOD FOR VALVE QUANTIFICATION

(71) Applicant: MATERIALISE N.V., Leuven (BE)

(72) Inventors: Nicolo Piazza, Montreal (CA); Peter Verschueren, Leuven (BE); Todd Pietila, Howell, MI (US)

(73) Assignee: MATERIALISE N.V., Leuven (BE)

( * ) Notice: Subject to any disclaimer, the term of this patent is extended or adjusted under 35 U.S.C. 154(b) by 0 days.

(21) Appl. No.: 15/312,106

(22) PCT Filed: May 20, 2015

(86) PCT No.: PCT/US2015/031811
§ 371 (c)(1),
(2) Date: Nov. 17, 2016

(87) PCT Pub. No.: WO2015/179543
PCT Pub. Date: Nov. 26, 2015

(65) Prior Publication Data
US 2017/0084029 A1    Mar. 23, 2017

Related U.S. Application Data

(60) Provisional application No. 62/001,016, filed on May 20, 2014.

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/1075* (2013.01); *G06T 7/60* (2013.01);
(Continued)

(58) Field of Classification Search
CPC . A61B 2576/023; A61B 5/055; A61B 5/1075; A61F 2/2496; G06T 17/10;
(Continued)

(56) References Cited

U.S. PATENT DOCUMENTS 8,812,431 B2 * 8/2014 Voigt ................. G06G 7/60
600/416
8,920,322 B2 * 12/2014 Mansi ................. A61B 8/0883
600/437
(Continued)

FOREIGN PATENT DOCUMENTS

WO    2010/067300 A1    6/2010

OTHER PUBLICATIONS

Andres Diaz Lantada et al., "Development of Personalized Annuloplasty Rings: Combination of CT Images and CAD-CAM Tools," Annals of Biomedical Engineering, Kluwer Academic Publishers-Plenum Publishers, NE, vol. 38, No. 2, Oct. 14, 2009, pp. 280-290, XP019765872.
(Continued)

*Primary Examiner* — Nirav G Patel
(74) *Attorney, Agent, or Firm* — Patterson & Sheridan LLP

(57) ABSTRACT

Systems and methods of valve quantification are disclosed. In one embodiment, a method of mitral valve quantification is provided. The method includes generating a 3-D heart model, defining a 3-D mitral valve annulus, fitting a plane through the 3-D mitral valve annulus, measuring the distance between at least two papillary muscle heads, defining an average diameter of at least one cross section around the micro valve annulus, and determining a size of an implant to be implanted.

25 Claims, 20 Drawing Sheets

(51) Int. Cl.
- *A61B 5/107* (2006.01)
- *G06T 7/62* (2017.01)
- *G06T 7/60* (2017.01)
- *G06T 17/10* (2006.01)
- *A61F 2/24* (2006.01)
- *A61B 5/055* (2006.01)

(52) U.S. Cl.
CPC ............... G06T 7/62 (2017.01); G06T 17/10 (2013.01); *A61B 5/055* (2013.01); *A61B 2576/023* (2013.01); *A61F 2/2496* (2013.01); *G06T 2207/20104* (2013.01); *G06T 2207/30048* (2013.01); *G06T 2210/41* (2013.01)

(58) Field of Classification Search
CPC . G06T 2207/20104; G06T 2207/30048; G06T 2210/41; G06T 7/0012; G06T 7/60; G06T 7/62
See application file for complete search history.

(56) References Cited

U.S. PATENT DOCUMENTS

| 9,956,046 B2 * | 5/2018 | Weber ................ A61B 34/10 |
| 2012/0053466 A1 | 3/2012 | Bianchi et al. |

OTHER PUBLICATIONS

P. Blanke et al., "Assessment of aortic annulus dimensions for Edwards Sapien Transapical Heart Valve implantation by computed tomography: calculating average diameter using a virtual ring method," European Journal of Cardio-Thoracic Surgery, Springer Verlag, Berlin,DE, vol. 38, No. 6, Dec. 1, 2010, pp. 750-758, XP027527253.

J. Ender et al., "Prediction of the annuloplasty ring size in patients undergoing mitral valve repair using real-time three-dimensional transoesophageal echocardiography," European Journal of Echcardiography, vol. 12, No. 6, May 4, 2011, pp. 445-453, XP05521585.

J. Ender et al., "Value of Augmented Reality-Enhanced Transesophageal Echocardiography (TEE) for Determining Optimal Annuloplasty Ring Size During Mitral Valve Repair," The Annals of Thoracic Surgery, Elsevier, USA, vol. 86, No. 5, Nov. 1, 2008, pp. 1473-1478, XP025560424.

Chandrajit Bajaj et al., "Multi-component heart reconstruction from volumetric imaging," Proceedings of the 2008 ACM Symposium on Solid and Physical Modeling, SPM '08, Jan. 1, 2008, p. 193, XP055117373, New York, New York, USA.

Ramon Casero et al., "Cardiac valve annulus manual segmentation using computer assisted visual feedback in three-dimensional image data," 2010 Annual International Conference of the IEEE Engineering in Medicine and Biology Society: (EMBC 2010); Buenos Aires, Argentina, Aug. 31-Sep. 4, 2010, IEEE, Piscataway, NJ, USA, Aug. 31, 2010, pp. 738-741, XP031883146.

* cited by examiner

SYSTEM AND METHOD FOR VALVE QUANTIFICATION

BACKGROUND OF THE INVENTION

Field of the Invention

This application relates to quantification of space and volume of areas in a patient's anatomy. In some aspects, this application relates specifically to mitral valve quantification. Even more specifically, this application relates to a system and method for quantifying the mitral valve apparatus and its surroundings for use in selecting an appropriately sized valve in a catheter-based transcatheter mitral valve repair procedure.

Description of the Related Technology

The human heart is a complex organ having many working parts which are critical to the proper functioning of the heart and the blood circulation and provides throughout the human body. The human heart is generally made up of four hollow chambers, the right atrium, the right ventricle, the left atrium, and the left ventricle. One of the keys to a properly functioning heart is the regulation of blood flow through these chambers. Regulation of blood throw through and between these chambers is provided by valves. For example, between the right atrium and the right ventricle, there is an atrioventricular opening.

The tricuspid valve is situated at that opening, and permits blood to move from the right atrium into the right ventricle. The valve opens when the blood pressure on the atrium site is greater than that on the ventricular side. When the valve opens, blood is permitted to flow from the right atrium into the right ventricle. When blood pressure is greater on the ventricle side, the valve closes. When the valve closes, blood is prevented from moving back in the other direction.

In the healthy heart, blood flow is also regulated between the left atrium and left ventricle. Here, the mitral valve allows blood to enter the left ventricle from the left atrium when the left atrium fills with blood and the pressure within the left atrium increases to a level above that of the left ventricle. When open, blood flows in a downward direction from the left atrium into the left ventricle, where it is pushed out to the rest of the body as part of the greater circulatory process. When a healthy mitral valve closes, blood flow between the two chambers stopped, and this closing prevents a reversal of blood flow.

Unfortunately, mitral valves do not always function normally. An abnormally functioning mitral valve can lead to severe health problems. One abnormality associated with the mitral valve is mitral regurgitation ("MR"). Mitral regurgitation is a disorder in which the mitral valve does not close properly during contraction of the left ventricle. This causes blood that has passed from the left atrium into the left ventricle to reverse its flow back into the left atrium.

Mitral regurgitation may be treated surgically. One surgical option includes the replacement of the mitral valve where the mitral valve is replaced with either a bio prosthetic replacement or a synthetic replacement. Another surgical option includes repair of the mitral valve. Although mitral valve repair is generally seen as preferable to mitral valve replacement due to the less invasive nature of the procedure, at present, both options require open-heart surgery. Because many candidates for mitral valve replacement and repair are not good candidates for tolerating the stress of open-heart surgery, there has been ongoing research directed to developing transcatheter mitral valves. These transcatheter mitral valves can be introduced using a catheter-based system, obviating the need for a surgical procedure. Using noninvasive catheter-based implant techniques, the physical trauma associated with an open heart surgery may be minimized and more patients may be treated effectively for the mitral regurgitation disorder.

Although the use of transcatheter mitral valves shows great promise, there are significant challenges involved with effectively deploying these types of devices. In an open surgical procedure, the surgeon has complete access to the surgical site. Consequently, the surgeon is able to visually survey the site in order to perform the procedure effectively. When using the catheter-based system, however, the surgeon must rely and various imaging technologies to provide guidance to positioning and fit of a repair and/or replacement valve. Because transcatheter mitral valves are inserted using a delivery catheter, it is critical that the transcatheter mitral valve introduced into the patient have an appropriate size and shape to conform to the patient's anatomy. The need for appropriate sizing and shaping of implants extends well beyond mitral valve-related procedures, and may be useful in various different surgical contexts. At present, methodologies for quantifying the pertinent measurements of the mitral valve are inadequate. Accordingly, there is a need for a standardized measurement method which can be used for planning implantation of medical devices, including transcatheter mitral valve implantation.

SUMMARY

In one embodiment, a method of method of mitral valve quantification is provided. The method may include generating a three-dimensional heart model and defining a three-dimensional mitral valve annulus. The method may further include fitting a plane through the three-dimensional mitral valve annulus. The distance between at least two papillary muscle heads may then be measured. The method further may include defining an average diameter of at least one cross section around the micro valve annulus. Based on the average diameter, a size of an implant may be selected.

In another embodiment, a computer-readable medium having computer-executable instructions stored thereon is provided. When the instructions are executed by a processor of a computing device, they cause the computing device to perform a method of mitral valve quantification. The method may include generating a three-dimensional ("3-D") model of a patient's heart from scanned images of the patient's heart and defining a 3-D mitral valve annulus. The method may also include fitting a plane through the 3-D mitral valve annulus. Distance may be measured between a first papillary muscle head and a second papillary muscle head in the 3-D model, and an average diameter of at least one cross section around the mitral valve annulus may be defined. The method may further include determining a size of an implant to be implanted.

DETAILED DESCRIPTION OF CERTAIN INVENTIVE EMBODIMENTS

As noted above, determining the appropriate dimensions for an implanted device can play an important role in the success of an implantation procedure. In the context of the transcatheter mitral valve repair, appropriate dimensions and sizing of the device plays an important role in the success of a transcatheter mitral valve repair procedure. Recognizing the importance of mitral valve quantification, the inventors have devised systems and methods which quantify the mitral valve in three-dimensions. The systems and methods typically provide for the calculation of a three-dimensional model of the blood volume in a patient's heart. From the three-dimensional model, a model of the myocardium and main anatomical structures in the heart can be also reconstructed. Using this reconstructed heart, a series of measurements may be performed from which a virtual insertion of a transcatheter mitral valve device can be simulated using three-dimensional computer modeling. Once the device has been virtually implanted within the three-dimensional heart model, the surgical site may be assessed by analyzing the potential impact of the device on anatomical structures could be harmed by physical features of the device. Based on that analysis, and appropriately sized mitral valve device can be selected for use in the repair procedure.

Figure 1:
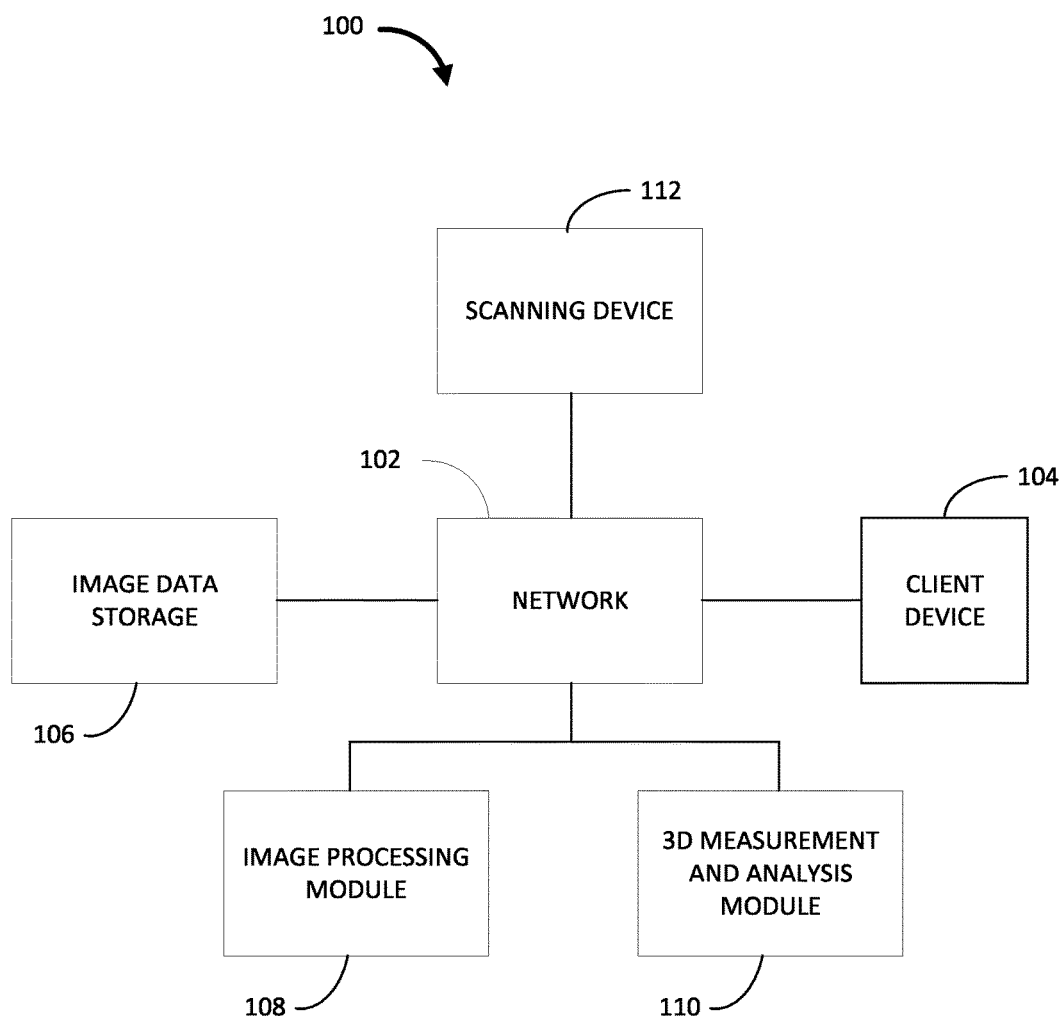
FIG. 1 is a block diagram of one example of a computing environment suitable for practicing various embodiments disclosed herein.

The systems and methods described herein may be implemented in a computing environment comprising one or more computing devices configured to provide various functionalities. FIG. 1 is an example of a computer environment 100 suitable for implementing certain embodiments described herein. The computer environment 100 may include a network 102. The network 102 may take various forms. For example, the network 102 may be a local area network installed at a surgical site. In some embodiments, the network 102 may be a wide area network such as the Internet, for e in other embodiments, the network 102 may be a combination of local area networks and wide area networks. Typically, the network will allow for secured communications and data to be shared between various computing devices. Among these computing devices are a client device 104. The client device 104 may be a typical personal computer device that runs an off-the-shelf operating systems such as Windows, Mac OS, Linux, Chrome, or some other operating system. The client device 104 may have application software installed to allow it to interact via the network 102 with other software stored on various other modules and devices in the computing environment 100. This application software may take the form of a web browser capable of accessing a remote application service. Alternatively, the application software may be a client application installed in the operating system of the client device 104. Client device 104 may also take the form of a specialized computer, specifically designed medical imaging work, or even more specifically for mitral valve quantification. The client device 104 may further take the form of a mobile device or tablet computer configured to communicate via the network 102 and further configured to run one or more software modules to allow a user to perform various methods described herein.

The computer environment 100 may further include image data storage 106. Typically, the image data storage 106 takes the form of a large database designed to store image files captured by a scanning device 112. These images may be DICOM images, or other types of images. The image data storage 106 may be part of a scanning device 112, or alternatively it may be part of a client computing device 104. The image data storage 106 may also be in a standalone database having dedicated storage optimized for medical image data. The computer environment 100 may also include a scanning device 112. The scanning device 112 may typically is a medical imaging device which scans a patient to create images of their anatomy. In the computing environment 100 shown in FIG. 1, the scanning device 112 may be a CT scanner or an MRI device. However, a skilled artisan will appreciate that other scanning technologies may be implemented which provide imaging data that can be used to create three-dimensional anatomical models.

As will be explained in detail below, the scanning device 112 may be configured to create cross-sectional images of a patient's heart. Those images may be stored in the image data storage 106, and utilized to create three-dimensional models of the heart. To that end, the computing environment 100 may also include an image processing module 108. The image processing module 108 may take the form of computer software, hardware, or a combination of both which retrieves the medical imaging data from image data storage 106 and generates a three-dimensional surface model using stacks of 2-D image data. The image processing module 108 may be a commercially available image processing software for three-dimensional design and modeling such as the Mimics application from Materialise NV. However, other image processing software may be used. In some embodiments, the image processing module 108 may be provided via a web-based network application that is accessed by a computer over the network (such as client device 104, for example). Alternatively, the image processing module may be a software application that is installed directly on the client device 104, and accesses image data storage 106 via the network 102. In general, the image processing module 108 may be any combination of software and/or hardware located within the computing environment 100 which provides image processing capabilities on the image data stored within the image data storage 106.

The computing environment also may include a three-dimensional measurement and analysis module 110 ("3-D measurement and analysis module"). The 3-D measurement and analysis module 110 may be software that is complementary to and/or bundled with the image processing module 108. For example, the 3-D measurement and analysis module 110 may be a bundled projects such as 3Matic® from Materialise NV. The 3-D measurement and analysis module may also take the form of general CAD and design software such as, for example, AutoCAD or SolidWorks. In some embodiments, the 3-D measurement and analysis module may be a specialized application created specifically for mitral valve quantification purposes. As will be explained in further detail below, the 3-D measurement and analysis module 110 will be generally used to determine precise measurements of various aspects of the patient anatomy in order to determine the appropriate dimensions for a surgical implant. In particular examples provided below, the heart anatomy is measured and in order to determine appropriate dimensions for a transcatheter mitral valve implant. As with the image processing module 108, the 3-D measurement and analysis module 110 may be a network-based application which is accessed via a web browser by one or more client devices 104. It may also be a native application installed into the operating system of a computer such as, client device 104 for example. In still other embodiments, the 3-D measurement and analysis module 110 may be a network application which is run as a client/server implementation.

Figure 2:
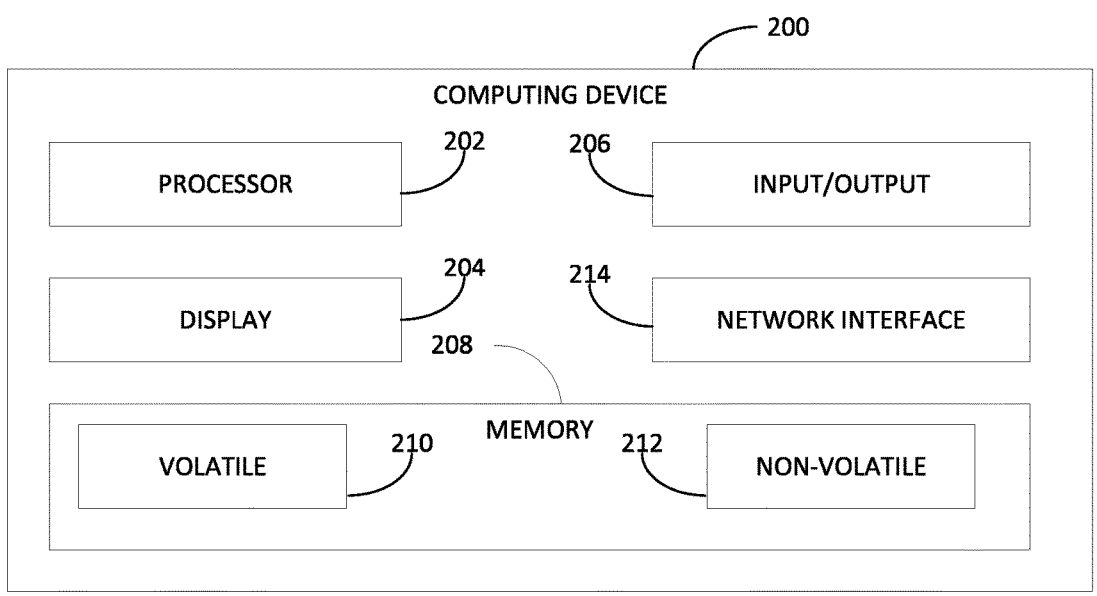
FIG. 2 is a high level system diagram of a computing system that may be used in accordance with one or more embodiments.

Various embodiments of the invention may be implemented using general and/or special purpose computing devices. Turning now to FIG. 2, an example of a computing device 200 suitable for implementing various embodiments of the invention is shown. The computer system 200 may generally take the form of computer hardware configured to execute certain processes and instructions in accordance with various aspects of one or more embodiments described herein. The computer hardware may be a single computer or it may be multiple computers configured to work together. The computing device 200 includes a processor 202. The processor 202 may be one or more standard personal computer processor such as those designed and/or distributed by Intel, Advanced Micro Devices, Apple, ARM, or Motorola. The processor 202 may also be a more specialized processor designed specifically for image processing and/or analysis. The computing device 200 may also include a display 204. The display 204 may be a standard computer monitor such as, an LCD monitor as is well known. The display 204 may also take the form of a display integrated into the body of the computing device, for example as with an all-in-one computing device or a tablet computer.

The computing device 200 may also include input/output devices 206. These may include standard peripherals such as keyboards, mice, printers, and other basic I/O software and hardware. The computing device 200 may further include memory 208. The memory 208 may take various forms. For example, the memory 208 may include volatile memory 210. The volatile memory 210 may be some form of random access memory, and may be generally configured to load executable software modules into memory so that the software modules may be executed by the processor 202 in a manner well known in the art. There he software modules may be stored in a nonvolatile memory 212. The nonvolatile memory 212 may take the form of a hard disk drive, a flash memory, a solid state hard drive or some other form of non-volatile memory. The non-volatile memory 104B may also be used to store non-executable data, such database files and the like.

The computer device 200 also may include a network interface 214. The network interface may take the form of a network interface card and its corresponding software drivers and/or firmware configured to provide the system 200 with access to a network (such as the Internet, for example). The network interface card 214 may be configured to access various different types of networks, such as those described above in connection with FIG. 1. For example the network interface card 214 may be configured to access private networks that are not publicly accessible. The network interface card 214 may also be configured to access wireless networks such using wireless data transfer technologies such as EVDO, WiMax, or LTE network. Although a single network interface 214 is shown in FIG. 2, multiple network interface cards 214 may be present in order to access different types of networks. In addition, a single network interface card 214 may be configured to allow access to multiple different types of networks.

In general, the computing environment 100 shown in FIG. 1 may generally include one, a few, or many different types of computing devices 200 which work together to carry out various embodiments described below. A skilled artisan will readily appreciate that various different types of computing devices and network configurations may be implemented to carry out the inventive systems and methods disclosed herein.

Figure 3:
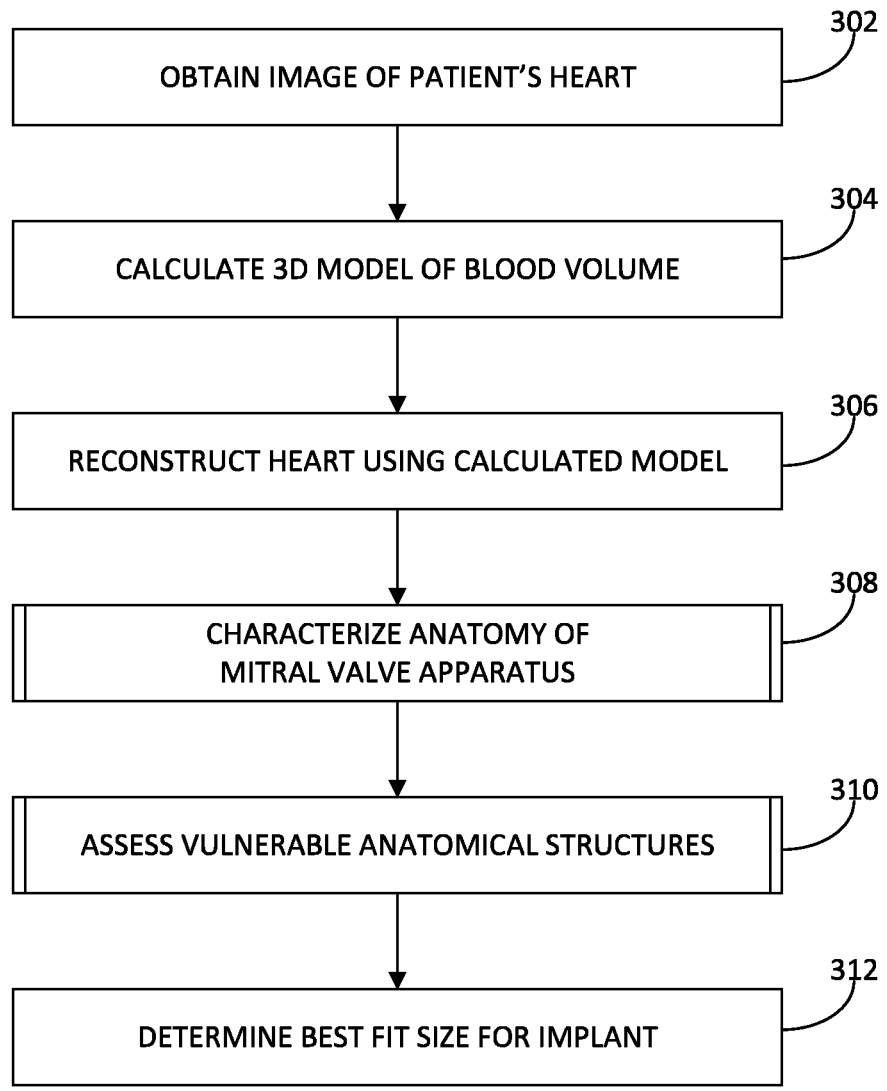
FIG. 3 is a flowchart showing an example of a method of providing mitral valve quantification according to one or more embodiments.

FIG. 3 is a high level flow diagram showing a process by which quantification of space and/or volume of a particular area of a patient's anatomy, in this example the mitral valve, may be realized according to one or more embodiments. Process begins at block 302, wherein image of the patient's heart acquired. The image may be acquired using the scanning device 112 shown in FIG. 1, such as a CT scanner or an MRI machine. In acquiring the image, a contrast agent may be used in order to improve the visibility of various internal structures of the heart. The image (or images) acquired using the scanning device 112 may be stored in image data storage 106 or some other computer memory accessible via the computer network 102. The process then moves to block 304. There a 3-D model of blood volume is calculated based on the acquired image. The use of a contrast agent in the previous step allows for the 3-D modeling of the blood volume. The 3-D model may be calculated using the image processing module 108, or some other software and/or hardware designed to generate 3-D models from CT and/or MRI image data.

Using the 3-D model of the blood volume, the anatomical structures of the heart may be reconstructed at block 306. Typically, it is easier to first obtain the blood volume from the clearly visible contrast agent and then use that to create the myocardium. However, a skilled artisan will appreciate that it is also possible to directly create the myocardial model. This reconstruction may also be performed using the image processing module 108. The reconstruction of the heart anatomy typically begins with segmentation of the left side of the heart, followed by optimization of the segmented and reconstructed 3-D model using optimization tools such as wrapping functions and smoothing functions to clean the surfaces of the models.

The process next moves to block 308. There, the anatomy of the mitral valve apparatus is characterized by defining control points and taking measurements of relevant anatomical structures. Typically, these measurements are performed using the 3-D measurement and analysis module 110. As discussed above, this 3-D measurement and analysis module 110 may be software that is bundled or even integrated with the image processing module 108. These measurements may include various steps. For example, using the 3-D measurement and analysis module 110, control points may be placed on the 3-D model of the heart which define the mitral valve annulus. These control points may be defined using a spline drawing function provided by the 3-D measurement and analysis module 110.

With the mitral valve annulus defined, the measurements may further include calculation of the 3-D surface area of the mitral valve annulus based on the spline. Additional measurements and analysis may be performed relating to the mitral valve annulus. For example, and as will be discussed below, one or more planes can be fit through the mitral valve annulus using the 3-D measurement and analysis module. Using these defined planes, additional measurements can be taken which help to more precisely define the actual geometry of the mitral valve annulus.

Once the measurements have been taken, the process then moves to block 310. There is an assessment is made of vulnerable anatomical structures. An anatomical structure may be vulnerable because a transcatheter mitral valve implant will not typically be fixed within the mitral valve. Rather, the mitral valve apparatus will experience a high degree of mobility. This movement can potentially damage surrounding anatomical structures from either collisions or protrusions from the device. This assessment may be made based on the measurements taken in the previous step. Moreover, it may further be a visual assessment. Finally, at block 312, based on the measurements taken and the assessed vulnerabilities, and appropriately sized mitral valve device may then be selected.

Figure 4:
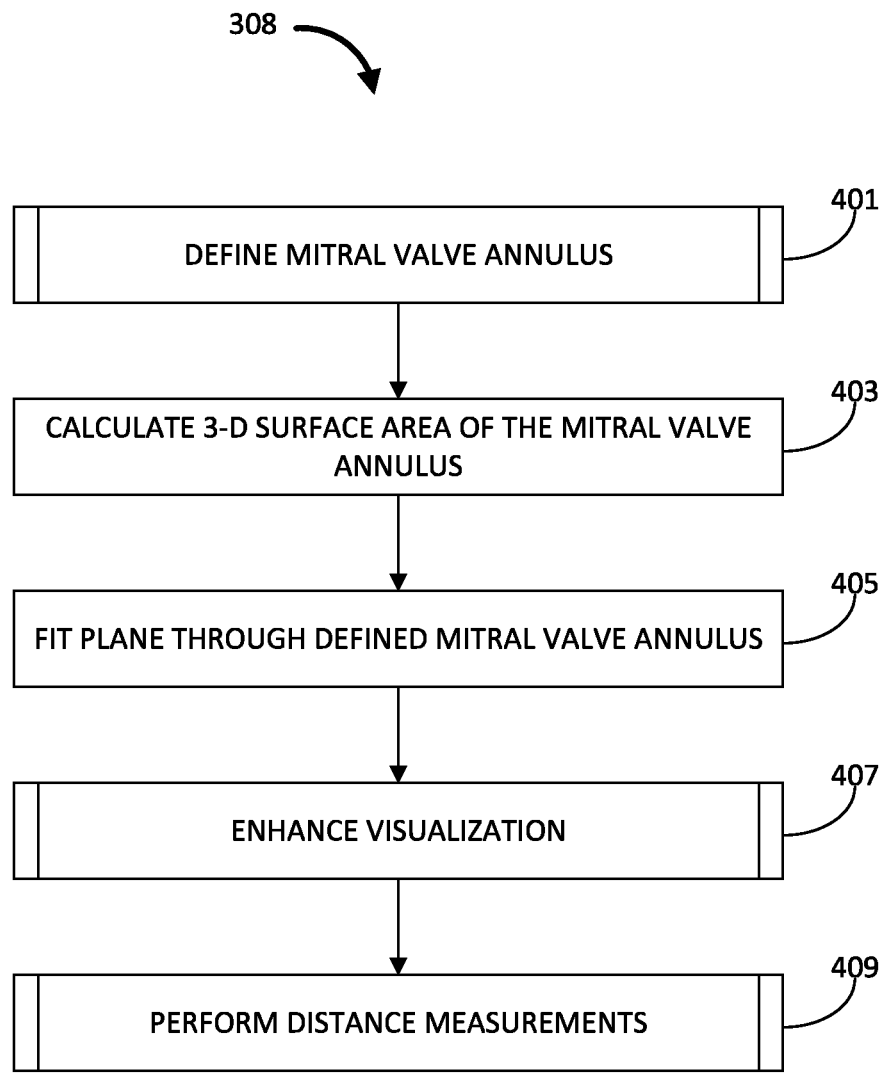
FIG. 4 is a flowchart of a sub process showing a more detailed view of the anatomical characterization of the mitral valve apparatus from FIG. 3 according to one embodiments.

As discussed above in connection with block 308 of FIG. 3, in certain embodiments, the mitral valve quantification process may include characterizing the anatomy of the mitral valve apparatus. FIG. 4 is a flow diagram providing one example of a sub process which may be implemented to characterize the anatomy is provided in block 308. The sub process begins at block 401 where, using the image processing module, the mitral valve annulus is defined within the reconstructed heart model. Additional details about how the mitral valve annulus is defined will be discussed in connection with FIG. 5 below. Once the mitral valve annulus has been defined, the process moves to block 403. There, the 3-D surface area of the mitral valve annulus is calculated. The process next moves to block 405 where a plane is fitted through the mitral valve annulus. In some embodiments, the plane may be generated by using a create datum plane function provided by the image processing module 108 and/or the 3-D measurement and analysis module 110. In fitting the plane through the mitral valve annulus, the 3-D surface area of the mitral valve annulus (the mitral surface) may be used as the fitting entity.

Next, the process moves to block 407. Here, the visualization of the 3-D heart model is enhanced by adding additional anatomical detail to the model and generating a view of a hollowed heart anatomy. Additional details about this enhancement of the visualization are provided below in connection with FIG. 6. Once the visualization of the 3-D model has been enhanced, the process then moves to block 409. At block 409, distance measurements are performed on the model in order to determine various dimensional attributes that may impact the size of the transcatheter mitral valve implant. These distance measurements may be performed against various aspects of the 3-D model, and are discussed in further detail below in connection with FIG. 8.

Figure 5:
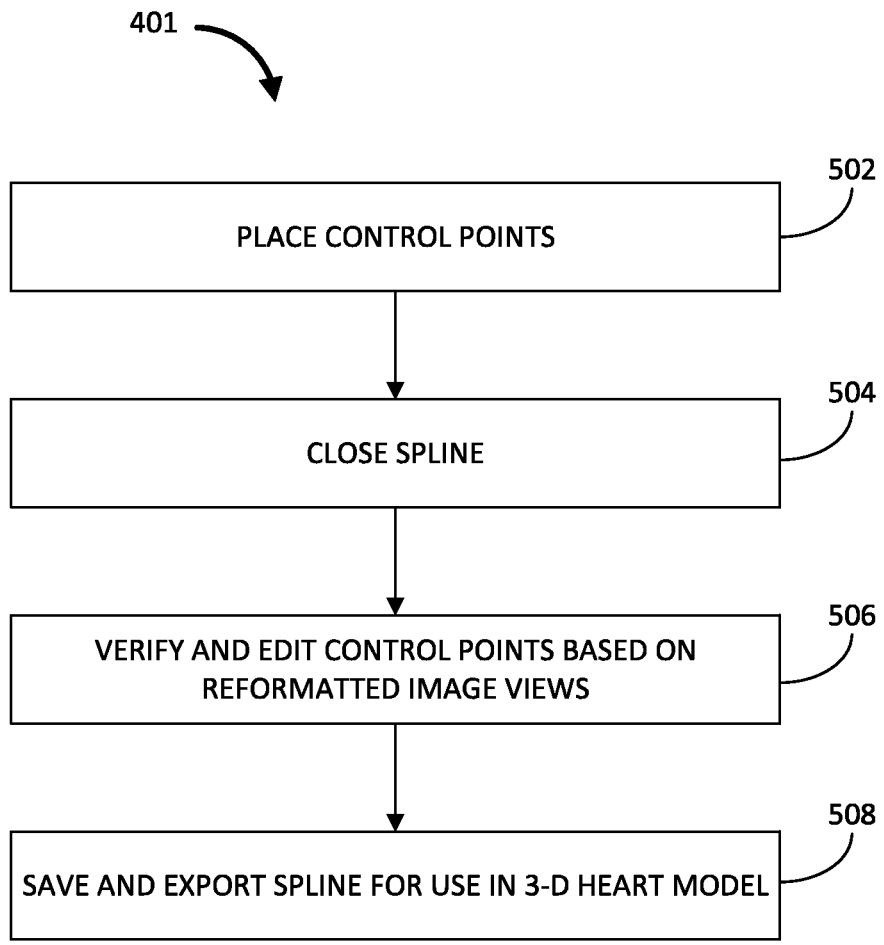
FIG. 5 is a flowchart showing an example of a process by which a mitral valve annulus may be defined as described in the process shown in FIG. 4.

As indicated above, FIG. 5 is a flow diagram which provides additional details about the process of defining the mitral valve annulus in the 3-D model. In this particular example, the mitral valve annulus may be defined by first placing control points on a user interface which graphically displays the 3-D model of the heart to the user. The control points may be placed using a spline drawing function provided by the 3-D measurement and analysis module 110. Once each of the control points for the defined mitral valve annulus have been selected, the initial control point may then be selected to close the spline at block 504. Once the spline has been closed, the process may then move to block 506 where the control points may be verified and edited based on reformatted image views generated from the data initially required by the scanning device 112. For example, the control points selected by the user may be superimposed on each of a coronal reformation, a sagittal reformation, as well as a conventional axial view. If the control points are inconsistent with the anatomy shown in any of the reformatted image views, they may be edited to ensure that they are consistent with the originally acquired image data. If the control points are consistent with the anatomy shown in the reformatted image views, then the process then may move to block 508 where the spline object is saved and exported for use in the 3-D heart model.

Figure 6:
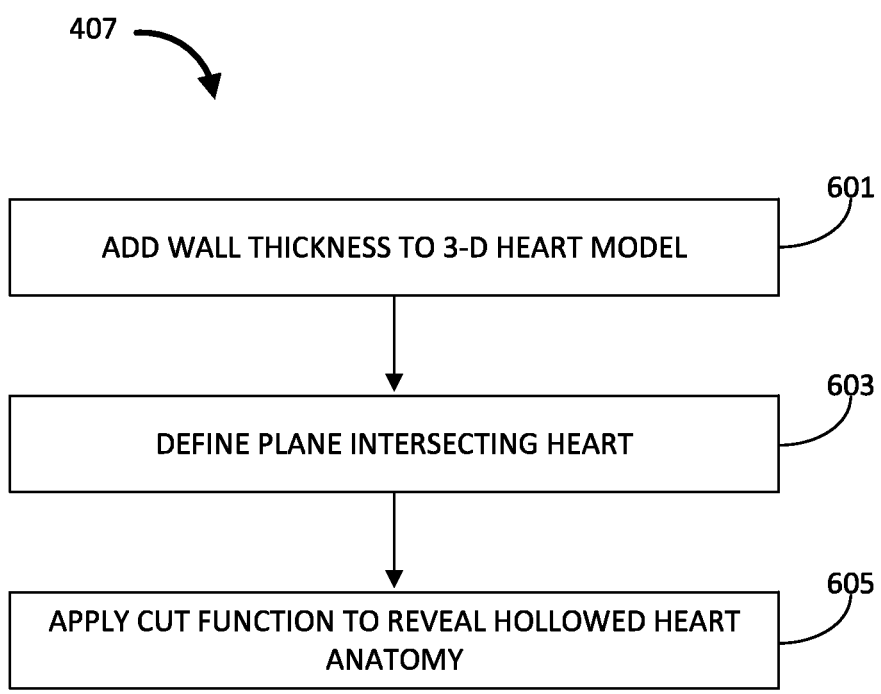
FIG. 6 is a flowchart providing a more detailed view of the visualization enhancement process from FIG. 4 according to one or more embodiments.

Turning now to FIG. 6, a more detailed flow diagram provides additional details about the visualization enhancement of block 407 and FIG. 4. In particular, FIG. 6 provides an example of one implementation of the visual enhancement process according to one embodiment. The process begins at block 601, where a wall thickness is added to the 3-D heart model. Because the original 3-D heart model was generated using images based on blood volume, those images do not account for wall thickness in the model. In some embodiments, the wall thickness may be added by applying a hollow operation to the heart model and specifying a wall thickness as part of that operation. Once the wall thickness has been added, the process may then move to block 603 where a plane intersecting the heart may be defined. In some embodiments, the plane may be used to section the anatomy to provide an internal view of the geometry of the left heart side. In one embodiment, a three point method may be implemented to define the plane which intersects the septum and the ascending aorta. However, a skilled artisan will appreciate that the precise location of the points can be modified, and that a skilled artisan, will appreciate however, that other methods of obtaining a view of the internal geometry may be utilized. Once the plane intersecting the heart has been defined, a cut function may then be applied to the hollowed heart anatomy at block 605. In applying the cut function to the hollowed heart anatomy, the defined plane on the septum may be used as the cutting entity. Applying the cut function results in a cutaway view of the interior of the heart anatomy.

Figure 7:
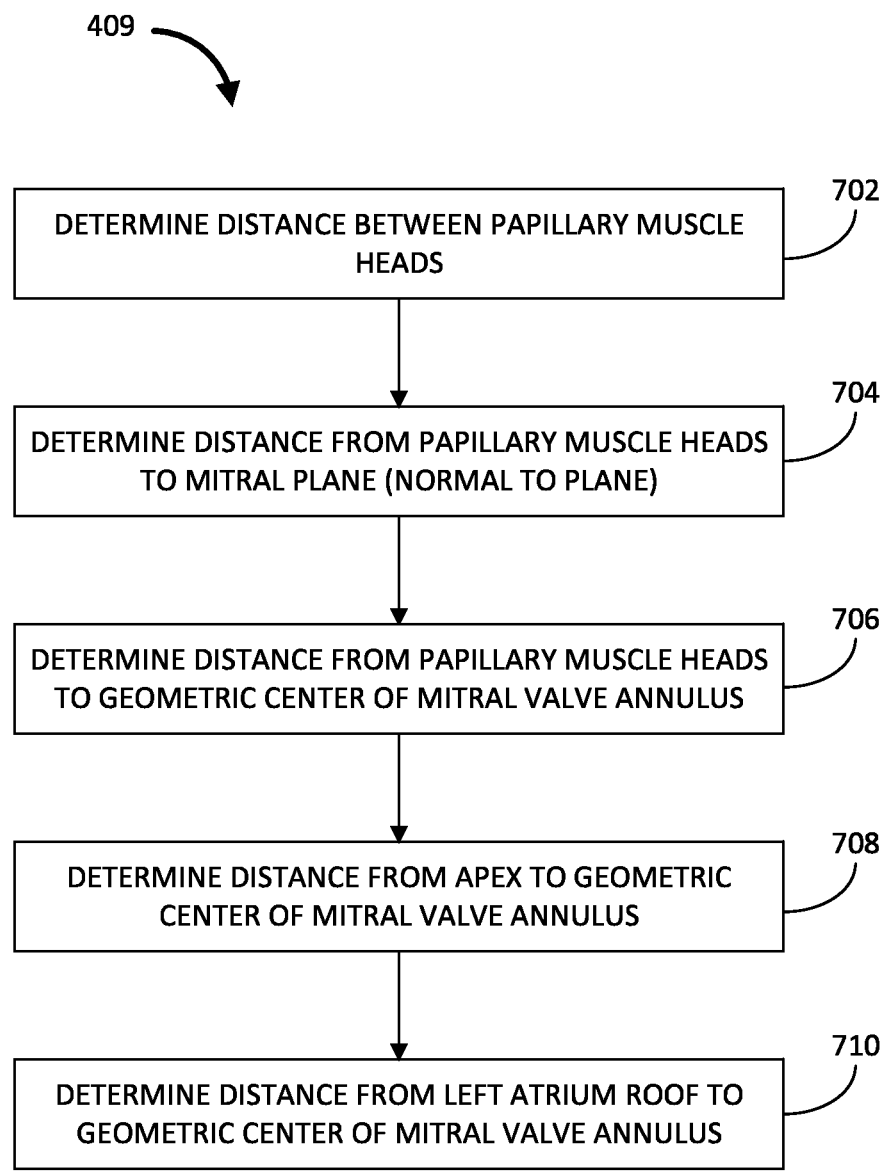
FIG. 7 is a flowchart providing additional detail about the distance measurement process described in FIG. 4.

FIG. 7 is a more detailed flowchart of the distance measurement step shown in block 409 of FIG. 4. In this example, various distance measurements may be taken using the 3-D measurement and analysis module 110. In this particular example, the process begins at block 702 where the distance between papillary muscle heads is determined. Utilizing the 3-D measurement and analysis module 110, a user may identify and select two points in the cutaway view generated by the cut function applied in FIG. 6. These two selected points may correspond to each of the papillary muscle heads. The 3-D measurement and analysis module 110 may, based on the location of these two points, determine the distance between the papillary muscle heads.

Next, the process moves to block 704. There the distance from each of the papillary muscle heads to the mitral plane is calculated. In this particular example the distance is calculated normal to the mitral plane, and not at the geometric center of the plane. Additional measurements may also be performed. The process next they move to block 706 where the distance from the papillary muscle heads to the geometric center of the mitral valve annulus is calculated. Next the process moves to block 708 where the distance from the apex of the heart to the geometric center of the mitral valve annulus is determined. The process then moves to block 710, where the distance from the left atrium roof to the geometric center of the mitral valve annulus is calculated.

These distance measurements can be used to select an implant design which avoids collisions with various anatomical structures after implantation. A transcatheter mitral valve implant may include various metallic components. When implanted into the mitral valve annulus, it takes a specific height and shape. The height and shape of the implanted device may interact substantially with several anatomical structures within the patient. For example, on the atrial side, the implant could collide with touch and possibly damage the thin walls of the atrium. In particular, the contours of the implant could potentially puncture the atrial wall because of its high mobility and deformation between systole vs diastole. In addition, on the ventricular side the deformations are also quite large, and the papillary muscles can interfere with the valves on the device by pushing against the frame of the valve. Additionally, they may even interfere with the new leaflets which are sewn into the metallic structure. This would mean the new valve would not be able to close or might even wear out faster because of this mechanical and repeatable contact. Accordingly, the distance measurements may be analyzed to account for the mobility of the device and select a size which will avoid these problems.

Figure 8A:
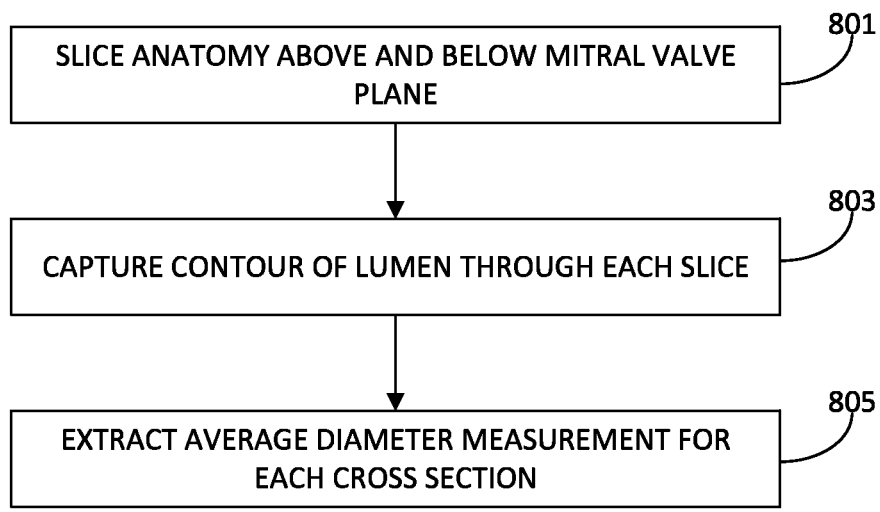
FIG. 8A is a flowchart showing a sub-process for the vulnerable anatomical structure assessment referenced at block 310 in FIG. 3.

Turning now to FIG. 8A, a more detailed flowchart is provided which provides an example of a detailed process for assessing vulnerable anatomical structures shown in FIG. 3. This sub-process begins at block 801. There using the 3-D measurement and analysis module 110, a user may slice the anatomy both above and below the mitral valve plane. In some embodiments, the translate function may be used to copy the mitral valve plane above and below the mitral valve annulus. In one specific implementation the plane may be translated at 5 mm increments up to 20 mm.

The process that moves to block 803 where the contour of the lumen (e.g., the mitral valve) is captured through each slice created using the translate function. In some embodiments, an intersection curve may be calculated between the blood volume anatomy provided by a 3-D model and each plane in order to capture the contour of the lumen through each slice. The process next moves to block 805, where the system may extract the average diameter measurements at each of the cross sections. In one embodiment, the average diameter measurements may be extracted using an arc method or some other function that can be used to create an arc or curve.

Figure 8B:
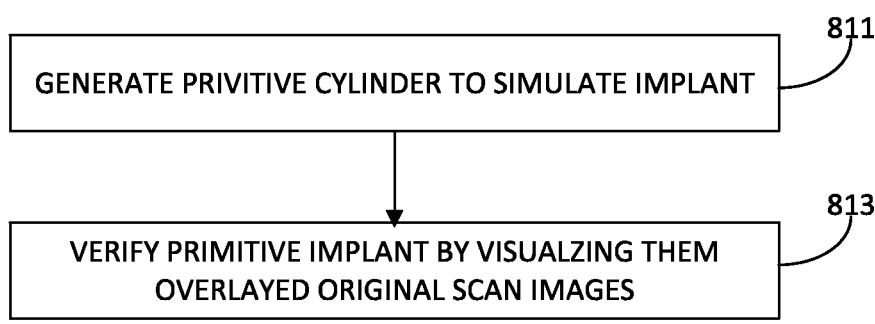
FIG. 8B is a flowchart showing an example of how the best fit size for an implant may be determined in accordance with one or more embodiments.

As discussed above in connection with FIG. 3, after vulnerable anatomical structures have been assessed, the size fit for a transcatheter mitral valve implant is determined. FIG. 8B is an example of a process by which the best size fit can be selected according to one or more embodiments.

The process begins at block 811, where a primitive cylinder may be generated to simulate the implant. The primitive cylinder may be generated based indirectly on the measurements determined in connection with FIG. 7, and also more directly based on the captured contour of the lumen of the mitral valve annulus obtained using the process described in connection with FIG. 8A above. Once the primitive cylinder has been created, the process then moves to block 813 where the primitive cylinder implant is verified by visualizing the contours of the objects overlaid on the original scanned images. Although the primitive generated in this example is a cylinder, a skilled artisan will readily appreciate that any number of other primitives may also be used separately or in combination with the cylinder.

Although the general process described in connection with FIG. 3 and the sub-processes described in connection with FIGS. 4-8B may be performed using various different configurations of computer hardware and/or software, FIGS. 9-14 provide examples of graphical user interfaces and computer generated images which may be utilized in performing the process described above.

Figure 9:
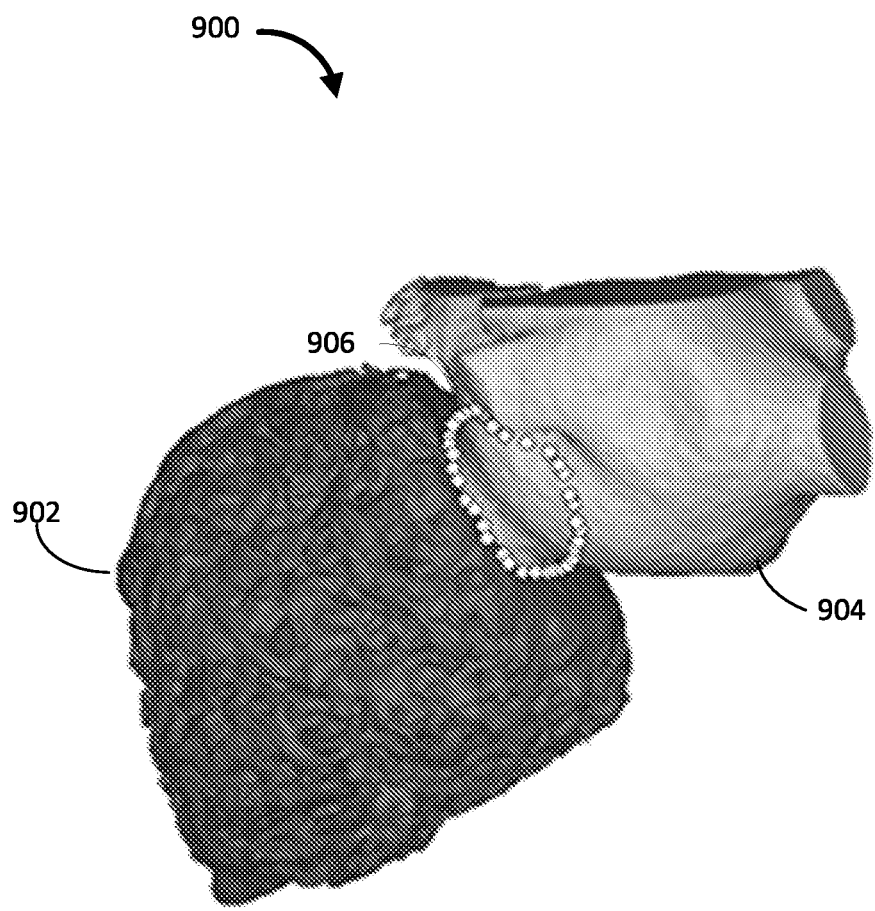
FIG. 9 is a an example of a graphical user interface environment which may be used to define the mitral valve annulus according to the process described in FIG. 5.

Turning now to FIG. 9, an example of a graphical user interface environment which may be used to define the mitral valve annulus as described above in connection FIG. 5. As shown, a 3-D surface model of the left side of the patient's heart is provided. Superimposed onto the 3-D surface model of the heart 900 is a spline 906 created using a spline drawing function provided by the image processing module 108. The spline 406 defines the mitral valve annulus and is created by the user inputting the control points shown enclosing the spline by selecting the initial control point.

Figure 10:
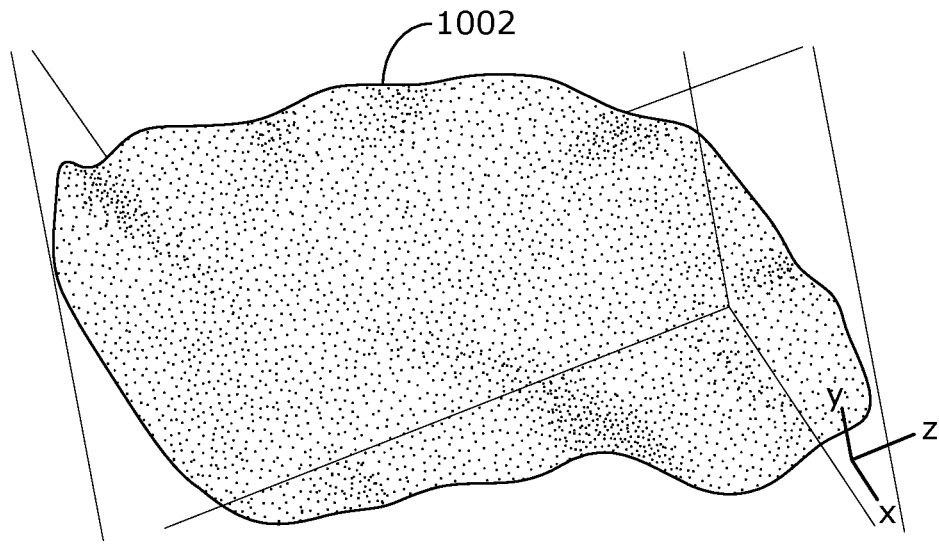
FIGS. 10-12 provide examples of graphical user interfaces which can be used to calculate the 3-D surface area of the mitral valve annulus and fit a plane through the annulus according to aspects of the process described in FIG. 4.
Figure 10:
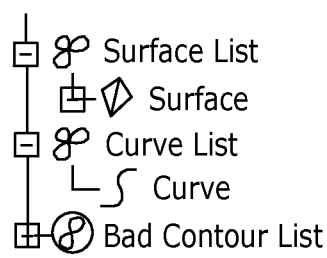
Figure 10:
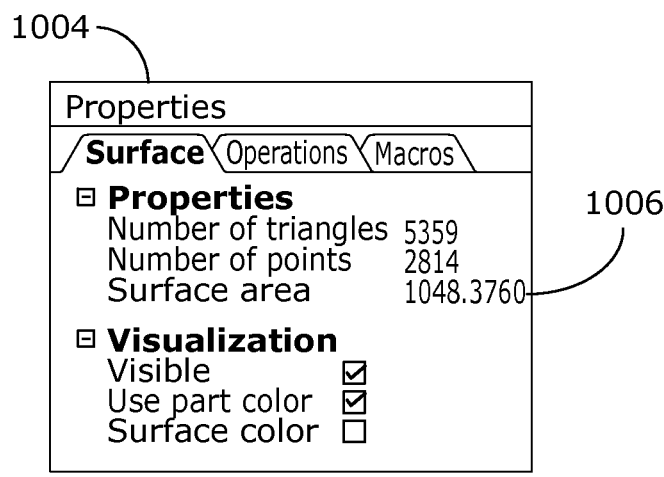
Figure 11A:
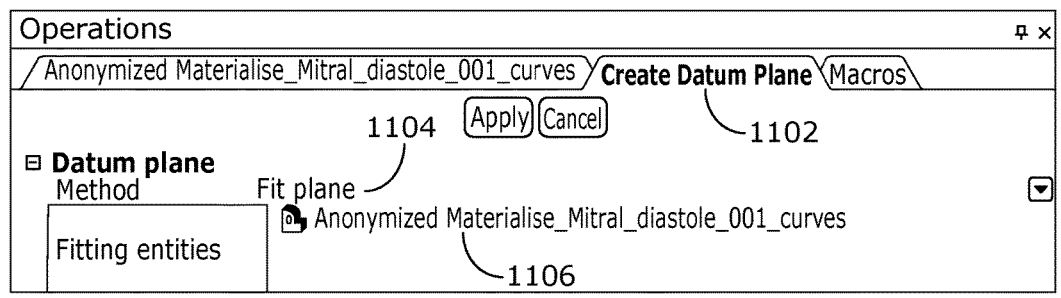
Figure 11B:
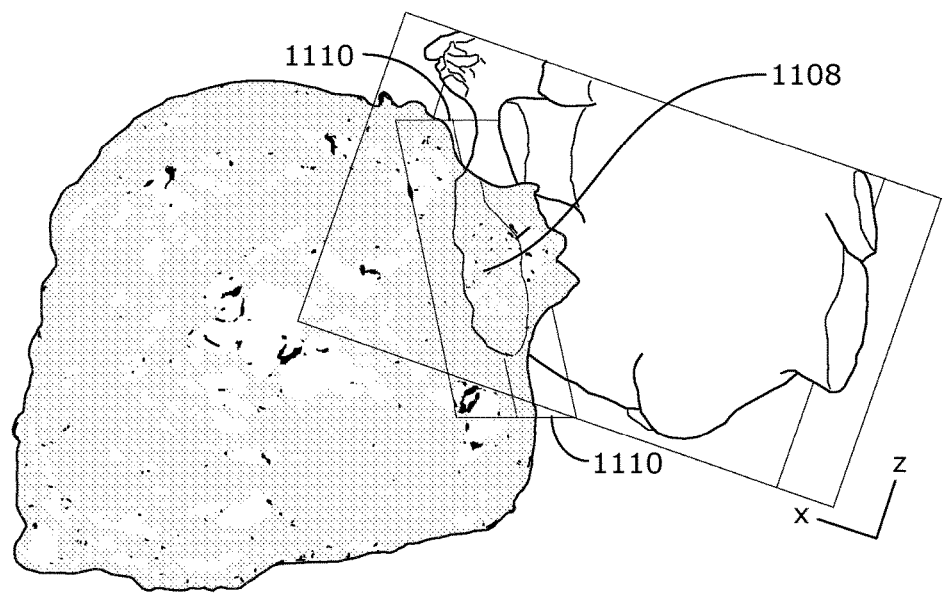
Figure 12:
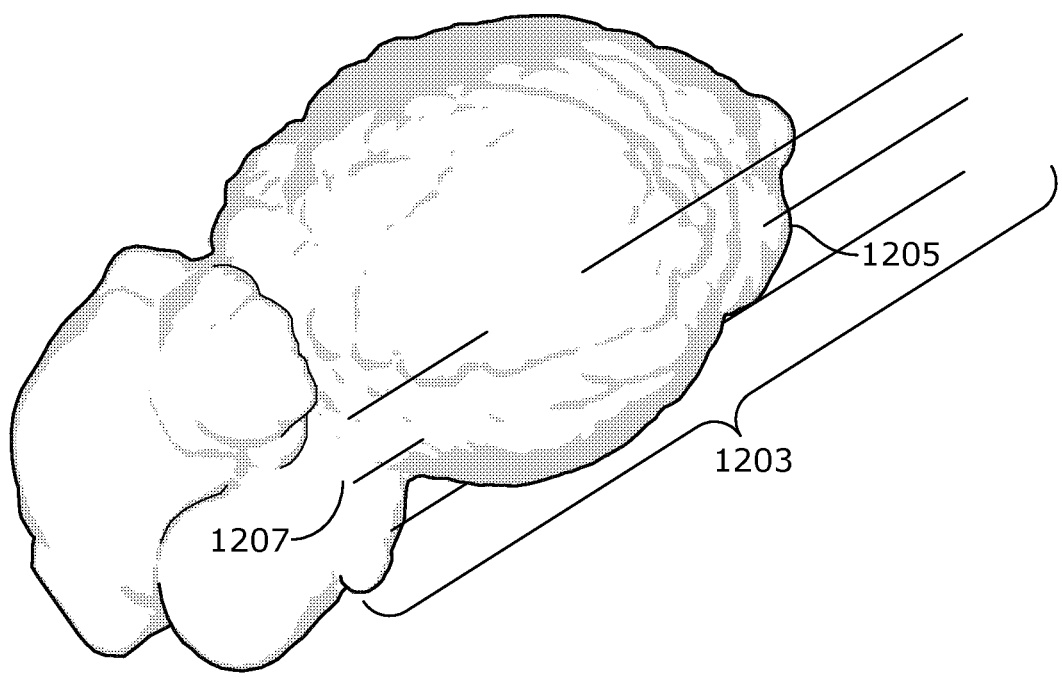

FIGS. 10-12 is an example of graphical user interface environment which can be used to calculate the 3-D surface area of the mitral valve annulus and fit a plane through the annulus as described above in blocks 403 and 405 of FIG. 4. FIG. 10 illustrates how the 3-D surface area of the mitral valve annulus is displayed. As shown the surface area 1002 of the mitral valve annulus is referenced and various properties 1004, including the calculated surface area 1006 are shown. The calculated surface area 1006 may be used to calculate the size of the implant device. In addition to the calculated surface area, the annulus projected circumference or a combination of other measurements may also govern the ultimate best fitting device.

FIGS. 11A and 11B provide graphical depictions of aspects of a user interface by which a plane may be fit through the mitral annulus using a create datum plane function. As shown, a create datum plane operation 1102 has been selected. A fit plane method 1104 for creating the datum plane has been selected, and the fitting entity 1106 has been chosen. In this particular case, the mitral surface from FIG. 10 has been selected as the fitting entity. FIG. 11B provides a graphical illustration of how the plane is fit onto the 3-D heart model. As shown, a plane has been fit through the mitral annulus, with the geometric center 1108 of the mitral valve annulus as the origin of the fit plane 1110.

As discussed above in connection with FIG. 6, wall thickness may be added to the 3-D heart model, and a plane may be defined intersecting the heart which can then be cut to reveal a hollowed heart anatomy. Turning now to FIG. 12, a graphical illustration is provided showing how the intersecting plane may be defined. Here, the intersecting plane 1203 is defined using a three point method which intersects the inter-ventricular septum 1205 (separating the left ventricle from the right ventricle) and ascending aorta 1207.

Figure 13:
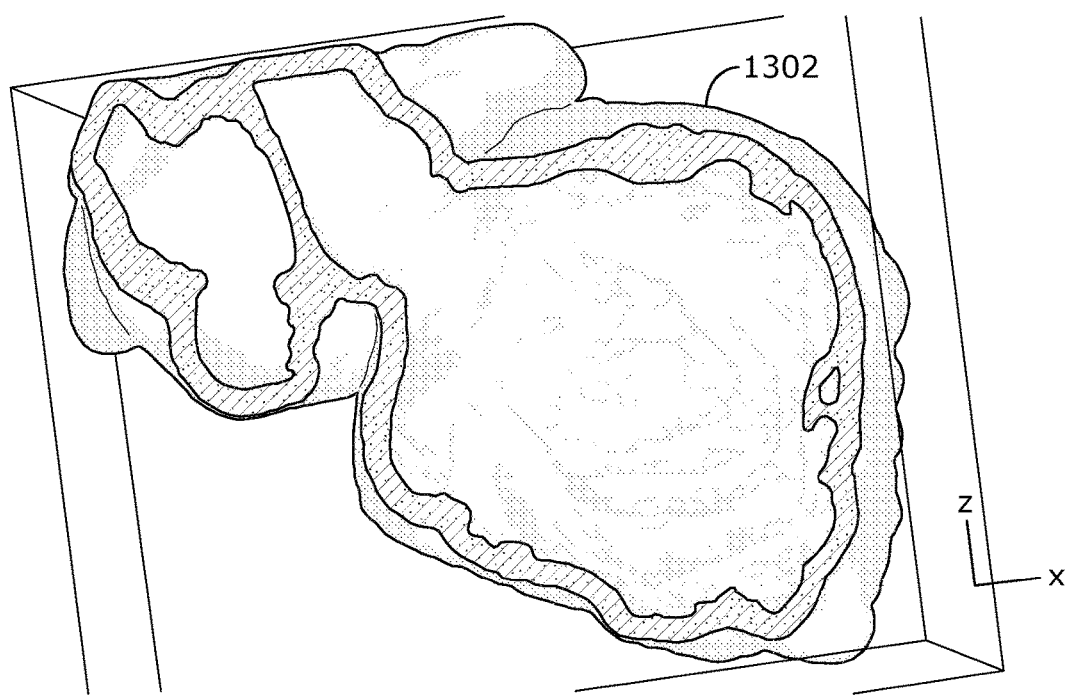
FIG. 13 is a graphical illustration of open hollowed heart anatomy constructed according to aspects of the process described in FIG. 6.

FIG. 13 provides a cutaway view 1302 of the 3-D heart model after the cut function has been applied to the hollowed heart anatomy as described at block 605 of FIG. 6. As discussed in connection with FIG. 6, in this particular example the defined plane shown in FIG. 12 has been used as the cutting entity.

Figure 14:
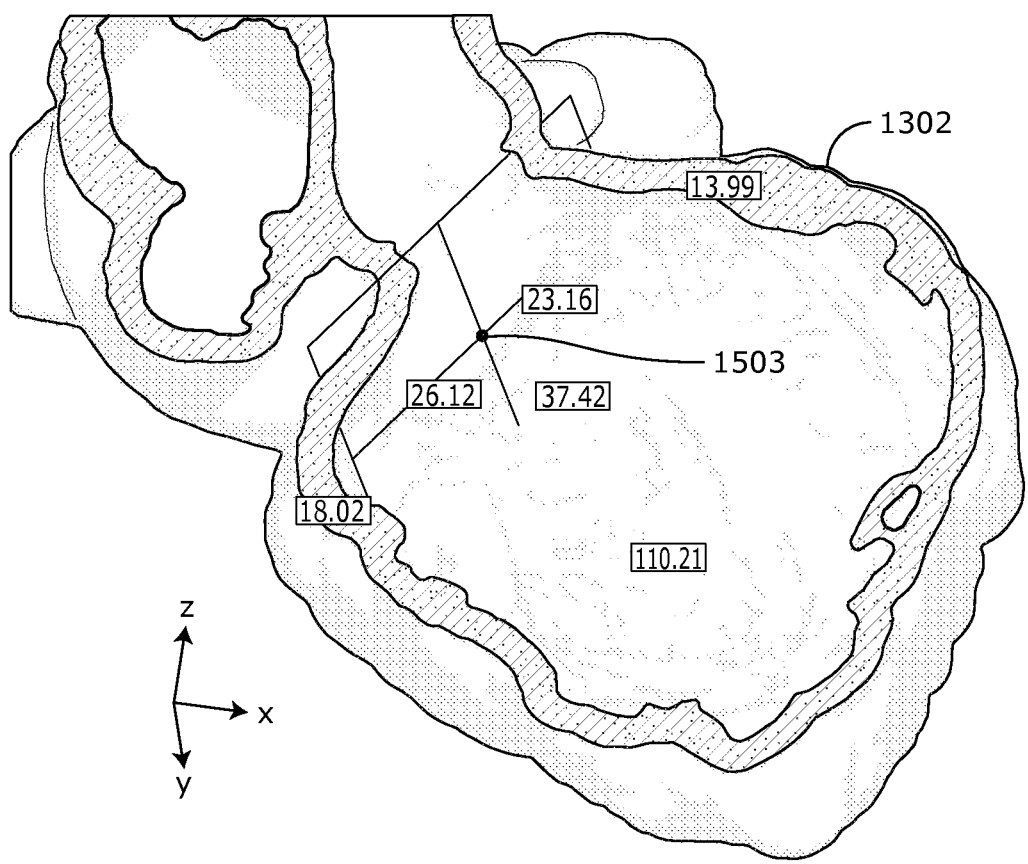
FIG. 14 is the open hollowed heart anatomy from FIG. 13 with various point to point measurements defined therein.

FIG. 14 provides a visual illustration of how the various measurements described in FIG. 7 may be carried out within a graphical user interface environment. FIG. 14 shows the cutaway view 1302 from FIG. 13. The cutaway view 1302 shows various measurements that have been extracted using a point-to-point measurement tool. Various measurements are shown with respect to the geometric center 1403 of the mitral annulus. Other measurements include the distance between the papillary muscle heads (37.42 mm), distance from the papillary muscle heads to the mitral plane (18.02 mm and 13.99 mm), the distance from the papillary muscle heads to the geometric center of the mitral valve annulus (26.12 mm and 23.16 mm), and the distance from the apex of the left ventricle to the geometric center of the mitral valve annulus (110.21 mm).

Figure 15:
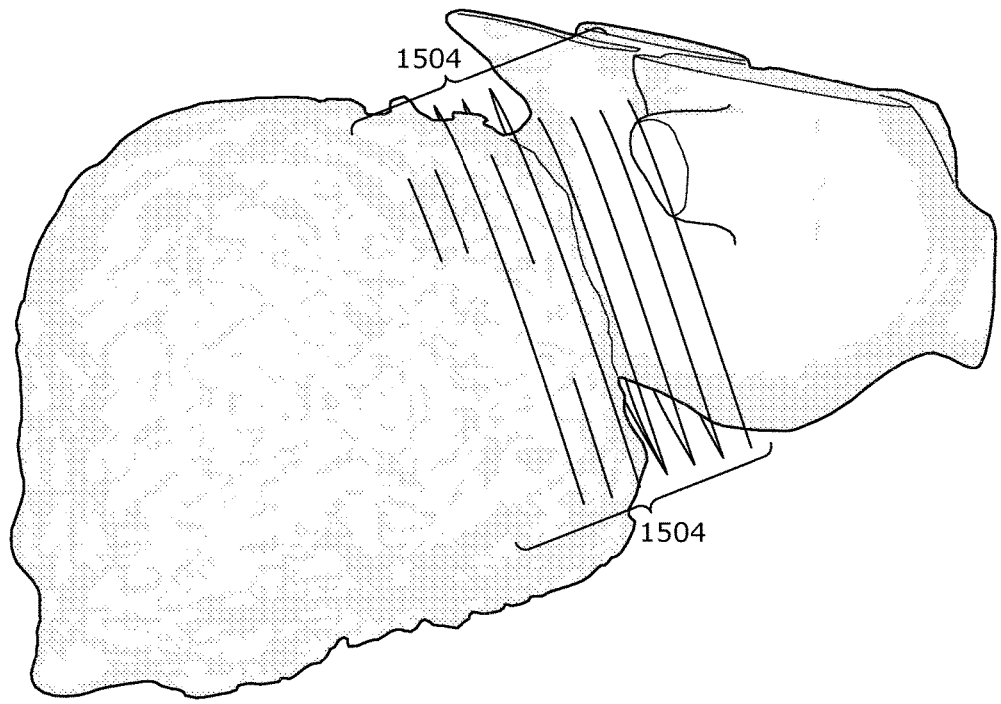
FIGS. 15 and 16 provide visual illustration of various aspects of the process described in connection with FIG. 8A.
Figure 15:
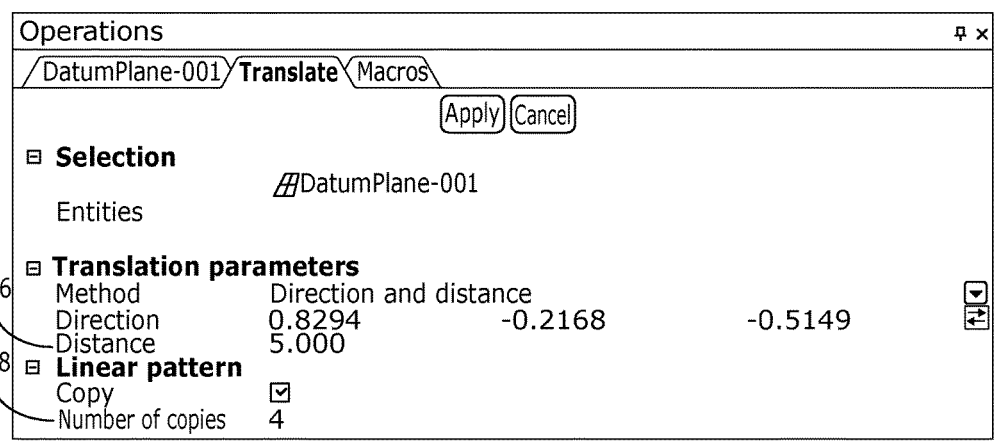
Figure 16:

Turning now to FIGS. 15 and 16, a visual illustration of the process described in FIG. 8A is provided. As shown, a Translate function three measurement and analysis module 110 has been used to copy the mitral valve plane 1504 above and below the annulus. The plane is translated at 5 mm increments to 20 mm as reflected by the values in the distance field 1506 and the number of copies field 1508. As noted above in FIG. 8A, an intersection curve may be calculated between the blood volume anatomy 302 and each plane 1504, thereby capturing the contour of the lumen through each slice. Turning now to FIG. 16, a graphical illustration is shown depicting how the average diameter measurement is extracted for each cross-section. As discussed above, these measurements may be extracted at these cross sections using an arc method.

Figure 17:
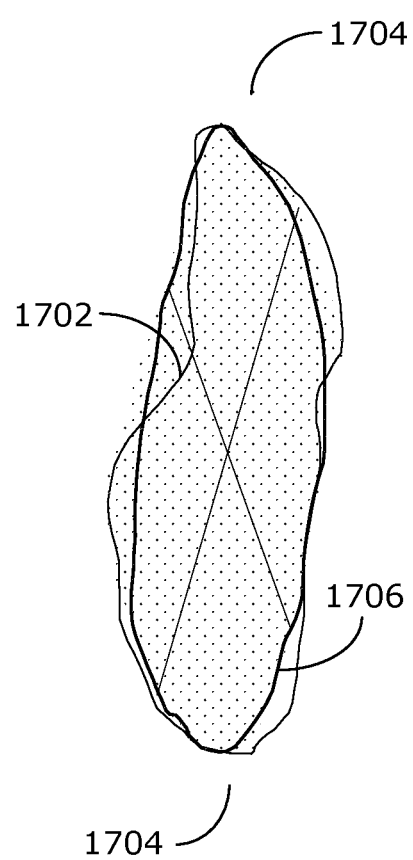
FIGS. 17-19C provide visual depictions of graphical user interface environments that may be used to simulate an implant using a primitive as described in connection with FIG. 8B above.

FIG. 17 provides a visual illustration of one graphical user interface environment that may be used to simulate an implant using a primitive cylinder as described in connection with FIG. 8B above. As shown, the mitral annulus curve 1702 is projected into the plane 1704 fit through the mitral annulus. The mitral annulus curve has been exported resulting in a flattened annulus 1706 and the diameter of the flattened annulus may be measured and used to size the primitive implant.

Figure 18A:
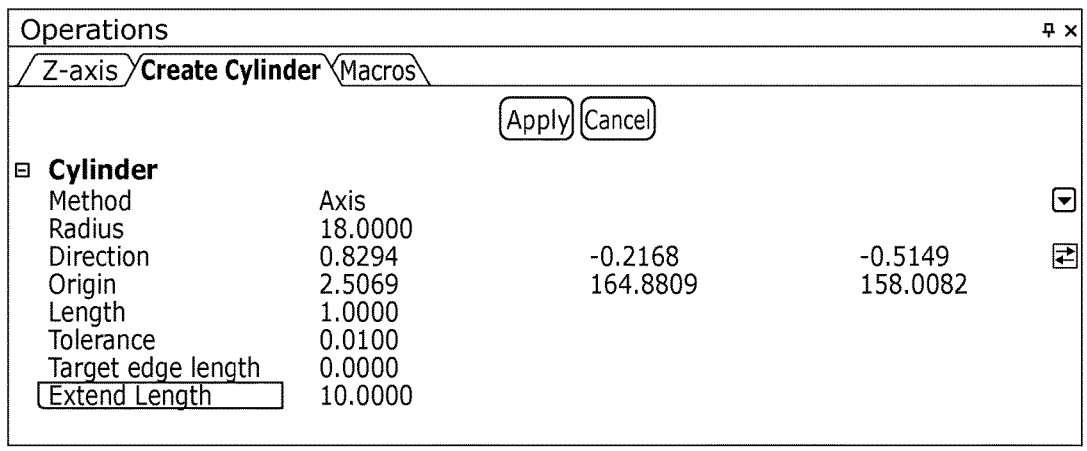
Figure 18B:
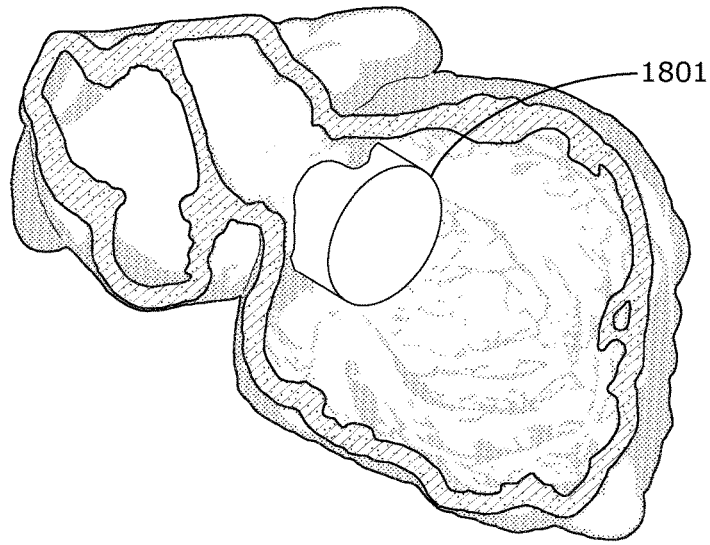

FIGS. 18A and 18B provide examples of a graphical user interface which may be used to create a simulated implant using a primitive cylinder. As shown in FIG. 18A, the create cylinder operation in the 3-D measurement and analysis module 110 is applied using the measurements obtained above. FIG. 18B shows the generated cylinder 1801 positioned within the mitral valve annulus.

Figure 19A:
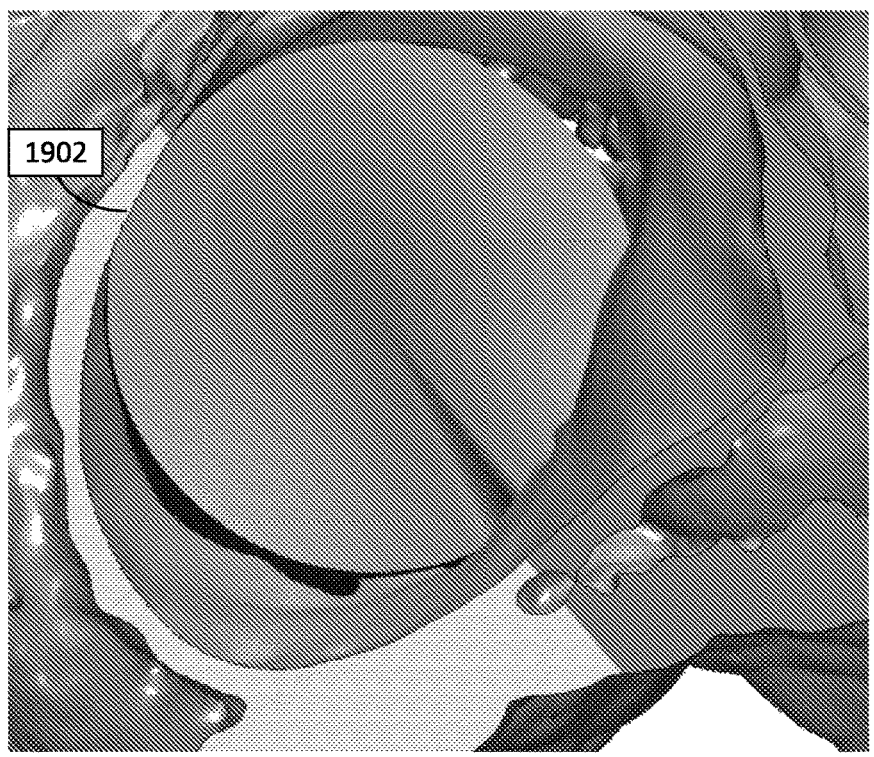
Figure 19B:
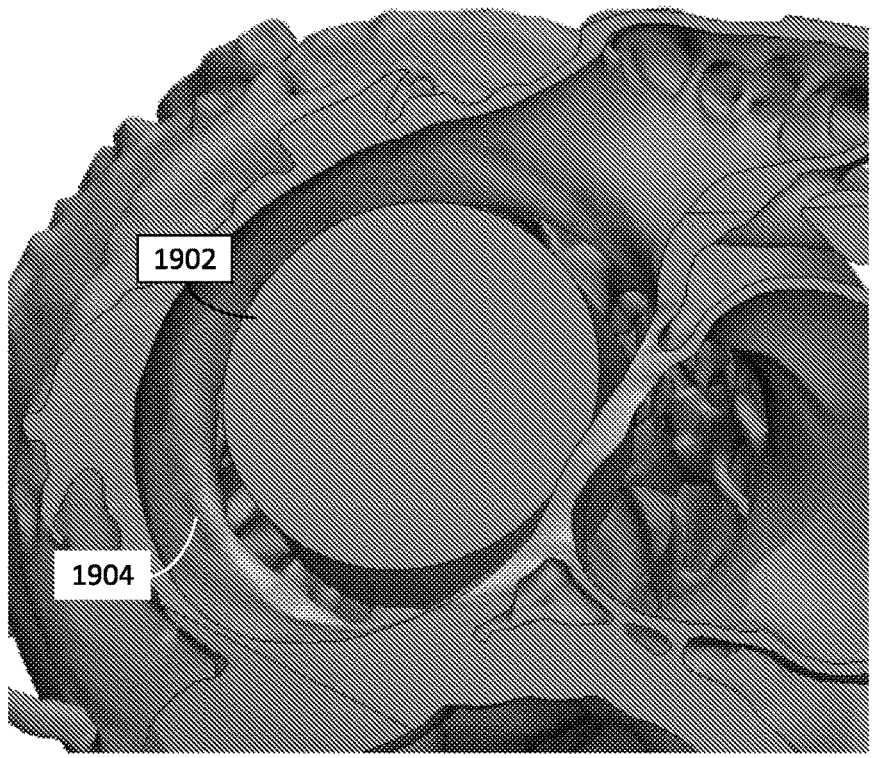
Figure 19C:
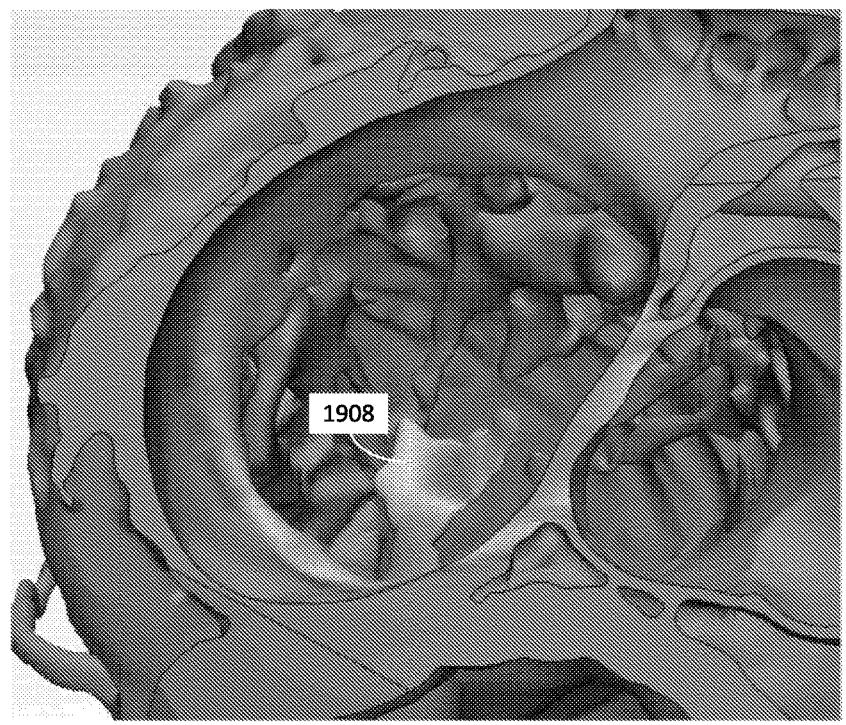

In some embodiments, the cylinder or some other type of geometry (e.g., primitive shape, CAD or scan file of the device as above) may be "virtually" implanted as shown in FIG. 19A. Here, a distance mapping may be performed with respect to the anatomy. This distance mapping may quantify the space that is available between the implanted device and each relevant item of anatomy. As shown a primitive 1902 (which in this example is a cylinder, but may take various other forms) has been virtually placed within the mitral valve annulus. Turning to FIG. 19B, a distance mapping is used to identify anatomical the position of anatomical structures in the heart (such as the walls of the atrium) or other anatomical features 1908 as shown in FIG. 19C. The distance mapping provides a clear visualization of the spacing between the proposed implant and the Using the systems and methods described above, a standardized method provides physicians and researchers the ability to quantify the mitral valve apparatus and its surroundings for transcatheter mitral valve repair research and development as well as determining the appropriate sizing in the context of patient and procedure planning. Although the particular examples above relate to quantification of the mitral valve, a skilled artisan will appreciate that the principles, systems, and methods described above can be readily applied in connection with other types of surgical procedures and other areas of the anatomy. For example, in some embodiments, the valve may be a pulmonary branch valve. In other embodiments, the the systems and methods described above may be used in the treatment of pulmonary artery stenosis. In other implementations, measurement and quantification of holes resulting from congenital heart defects, such as atrial septal defects ("ASDs") or ventricular septal defects (VSDs) may also be performed to select an appropriate size for a catheter implant or other device for implantation.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A computer-implemented method of determining a size of a valve implant to be implanted in an organ, the method comprising:
   generating on a computing device a digital three-dimensional ("3-D") model of the organ from scanned images of the organ;
   defining a 3-D valve annulus in the 3-D model;
   fitting a first plane through the 3-D valve annulus in the 3-D model;
   measuring a distance between a first location and a second location in the 3-D model;
   defining an average diameter of at least one cross section of the 3-D model around the valve annulus in a plane not coinciding with the first plane; and
   determining the size of the implant to be implanted based on the measured distance and the average diameter.

2. The method of claim 1, wherein the valve is a mitral valve, and wherein the organ is a patient's heart, and wherein measuring the distance between the first location and the second location comprises measuring the distance between a first papillary muscle head and a second papillary muscle head in the 3-D model.

3. The method of claim 2, wherein generating the 3-D model comprises:
   obtaining an image of the patient's heart;
   calculating a 3-D model of a blood volume of the patient's heart; and
   reconstructing the patient's heart using the calculated 3-D model of the blood volume.

4. The method of claim 2, wherein measuring distance between the first papillary muscle head and the second papillary muscle head comprises:
   defining a second plane through the 3-D model intersecting a septum and an ascending aorta of the patient's heart;
   applying a cut function along second plane to reveal a cutaway view of the patient's heart anatomy;
   performing the measuring using a point to point measurement tool.

5. The method of claim 2, further comprising:
measuring a distance from at least one papillary muscle head to the first plane;
measuring a distance from at least one papillary muscle head to a geometric center of the defined 3-D mitral valve annulus;
measuring a distance from a ventricular apex of the patient's heart to the geometric center of the defined 3-D mitral valve annulus;
measuring a distance from a left atrium roof to the geometric center of the defined 3-D mitral valve annulus; and
determining the size of the implant to be implanted based on the measured distances.

6. The method of claim 2, wherein measuring distance between the first papillary muscle head and the second papillary muscle head comprises:
adding wall thickness to the 3-D model;
visualizing the inside of the heart's anatomy;
performing the measuring using a point to point measurement tool.

7. The method of claim 1, wherein defining the 3-D valve annulus comprises:
placing control points on the 3-D model;
verifying the control points using one or more reformatted image views of the organ; and
storing the control points for use in the 3-D model.

8. The method of claim 7, wherein the control points comprise a spline, and wherein the spline is defined by selecting the control points.

9. The method of claim 2, wherein determining the size of the implant to be implanted comprises:
generating a cylinder to simulate the implant; and
verifying the cylinder by visualizing the cylinder overlaid on the scanned images of the organ.

10. The method of claim 9, wherein the scanned images of the organ are at least one of CT images and MRI images.

11. The method of claim 1, wherein defining the average diameter of at least one cross section of the 3-D model around the valve annulus in the plane not coinciding with the first plane comprises:
slicing the 3-D model above and below the first plane to obtain two or more cross-sections;
capturing a contour of lumen through each cross-section; and
extracting an average measurement for each cross-section.

12. The method of claim 11, wherein the average measurements are extracted using at least one of an arc method, a circle fit, an elliptical fit, and a freeform line segment fit.

13. The method of claim 1, wherein the valve is a pulmonary valve.

14. A non-transitory computer-readable medium having computer-executable instructions stored thereon, which, when executed by a processor of a computing device, cause the computing device to perform a method of determining a size of a valve implant to be implanted in an organ, the method comprising:
generating a digital three-dimensional ("3-D") model of the organ from scanned images of the organ;
defining a 3-D valve annulus in the 3-D model;
fitting a first plane through the 3-D valve annulus in the 3-D model;
measuring a distance between a first location and a second location in the 3-D model;
defining an average diameter of at least one cross section of the 3-D model around the valve annulus in a plane not coinciding with the first plane; and
determining the size of the implant to be implanted based on the measured distance and the average diameter.

15. The non-transitory computer-readable medium of claim 14, wherein the valve is a mitral valve, and wherein the organ is a patient's heart, and wherein measuring the distance between the first location and the second location comprises measuring the distance between a first papillary muscle head and a second papillary muscle head in the 3-D model.

16. The non-transitory computer-readable medium of claim 15, wherein generating the 3-D model comprises:
obtaining an image of the patient's heart;
calculating a 3-D model of a blood volume of the patient's heart; and
reconstructing the patient's heart using the 3-D model of the blood volume.

17. The non-transitory computer-readable medium of claim 15, wherein measuring the distance between the first papillary muscle head and the second papillary muscle head comprises:
adding wall thickness to the 3-D model;
visualizing the inside of the heart's anatomy; and
performing the measuring using a point to point measurement tool.

18. The non-transitory computer-readable medium of claim 15, further comprising:
measuring a distance from at least one papillary muscle head to the first plane;
measuring a distance from at least one papillary muscle head to a geometric center of the 3-D valve annulus;
measuring a distance from a ventricular apex of the patient's heart to the geometric center of the 3-D valve annulus;
measuring a distance from a left atrium roof to the geometric center of the 3-D valve annulus; and
determining the size of the implant to be implanted based on the measured distances.

19. The non-transitory computer-readable medium of claim 14, wherein defining the 3-D valve annulus comprises:
placing control points on the 3-D model, wherein the control points define the 3-D valve annulus;
verifying the control points using reformatted image views of the organ; and
storing the control points for use in the 3-D model.

20. The non-transitory computer-readable medium of claim 19, wherein the control points comprise a spline, and wherein the spline is defined by selecting the control points.

21. The non-transitory computer-readable medium of claim 14, wherein determining the size of the implant to be implanted comprises:
generating a cylinder to simulate the implant; and
verifying the cylinder by visualizing the generated cylinder overlaid on the scanned images of the organ.

22. The non-transitory computer-readable medium of claim 14, wherein the scanned images of the organ are at least one of CT images and MRI images.

23. The non-transitory computer-readable medium of claim 14, wherein defining the average diameter of at least one cross section of the 3-D model around the valve annulus in the plane not coinciding with the first plane comprises:
slicing the 3-D model above and below the first plane to obtain two or more cross-sections;
capturing a contour of lumen through each cross-section; and extracting an average diameter measurements for each cross-section.

24. The non-transitory computer-readable medium of claim 23, wherein the average diameter measurements are extracted using at least one of an arc method, a circle fit, an elliptical fit, and a freeform line segment fit.

25. The non-transitory computer-readable medium of claim 14, wherein the valve is a pulmonary valve.

\* \* \* \* \*